(12) United States Patent
Choi

(10) Patent No.: US 7,231,263 B2
(45) Date of Patent: Jun. 12, 2007

(54) METHOD FOR CONTROLLING INSULIN PUMP THROUGH INTERNET

(76) Inventor: Soo Bong Choi, Unit 5-908, Youwon Apartments 421-7 Yeonso-dong, Chungju-shi, Chungcheongbuk-do (KR)

( * ) Notice: Subject to any disclaimer, the term of this patent is extended or adjusted under 35 U.S.C. 154(b) by 0 days.

(21) Appl. No.: 11/546,110

(22) Filed: Oct. 10, 2006

(65) Prior Publication Data

US 2007/0032891 A1    Feb. 8, 2007

Related U.S. Application Data

(63) Continuation of application No. 10/852,375, filed on May 24, 2004, now abandoned.

(30) Foreign Application Priority Data

May 23, 2003   (KR) ...................... 10-2003-0033115

(51) Int. Cl.
G05B 11/00 (2006.01)
G05B 15/00 (2006.01)
G05B 19/18 (2006.01)
A61M 31/00 (2006.01)
A61M 37/00 (2006.01)

(52) U.S. Cl. ........................... 700/17; 700/19; 700/20; 700/65; 700/83; 604/65; 604/66; 604/67; 604/154

(58) Field of Classification Search ............ 700/17–20, 700/83, 65; 604/65–67, 154
See application file for complete search history.

(56) References Cited

U.S. PATENT DOCUMENTS 5,935,099 A * 8/1999 Peterson et al. .............. 604/65

| 6,689,091 B2* | 2/2004 | Bui et al. ...................... 604/67 |
| 6,768,425 B2* | 7/2004 | Flaherty et al. ........ 340/870.07 |
| 2002/0038392 A1* | 3/2002 | De La Huerga ............... 710/8 |
| 2002/0126036 A1* | 9/2002 | Flaherty et al. ............. 341/176 |
| 2003/0208113 A1* | 11/2003 | Mault et al. ................. 600/316 |
| 2004/0068230 A1* | 4/2004 | Estes et al. .................. 604/154 |
| 2004/0122353 A1* | 6/2004 | Shahmirian et al. .......... 604/65 |
| 2005/0065464 A1* | 3/2005 | Talbot et al. ................. 604/66 |

FOREIGN PATENT DOCUMENTS

KR   10-2003-0006078   *   8/2004

* cited by examiner

*Primary Examiner*—Anthony Knight
*Assistant Examiner*—Ronald D Hartman, Jr.
(74) *Attorney, Agent, or Firm*—Adams and Reese LLP

(57) ABSTRACT

A method for controlling an insulin pump through the Internet. The method comprises the steps of ascertaining whether a logged-in person is a physician; determining the logged-in person as a nurse when the logged-in person is not a physician, receiving a patient's blood sugar level data and generating a command to change an insulin injection amount; checking whether the logged-in person is an attending physician when the logged-in person is a physician, and changing the logged-in person to an attending physician when the logged-in person is not an attending physician; and driving a corresponding insulin pump having the patient's ID by transmitting through the Internet and Bluetooth modules a new prescription made in consideration of a current blood sugar level measurement and insulin injection amount, when the logged-in person is an attending physician or when the logged-in person is changed to an attending physician.

3 Claims, 11 Drawing Sheets

PRIOR ART

PRIOR ART

PRIOR ART

PRIOR ART

METHOD FOR CONTROLLING INSULIN PUMP THROUGH INTERNET

CROSS-REFERENCE TO RELATED APPLICATIONS

This application claims priority from Korean Patent Application No. 10-2003-0033115 filed on May 23, 2003.

STATEMENT REGARDING FEDERALLY SPONSORED RESEARCH OR DEVELOPMENT

Not Applicable

FIELD OF THE INVENTION

The present invention relates to a method for controlling an insulin pump through the Internet, wherein Bluetooth chips (or modules) capable of radio communication are respectively built in the insulin pump and a blood sugar level measuring device to drive the insulin pump through inter-communication and a separate Bluetooth communication device and a personal digital assistant (PDA) are linked with a server to control the individual insulin pump and blood sugar level measuring device.

DESCRIPTION OF THE RELATED ART

The diabetes is regarded as a representative disease of the $20^{th}$ century, which is incidental to civilization. One billion or more persons among a worldwide population of about sixty billions are suffering from the diabetes, and it is estimated in Korea that approximately two millions of people and ten percents of medical patients are diabetics. So far, the diabetes is regarded as a disease which is not completely cured but administrated to get better in its condition. If the administration is unsuccessful, a patient may lose his or her life due to various diabetes complications. In Korea, as a death rate owing to diabetes is increased to 11.5 persons per a hundred thousand people (statistics on 1990), the diabetes becomes an object of fear.

The diabetes is diagnosed when a blood sugar level exceeds 140 mg/dl on an empty stomach or is no less than 200 mg/dl two hours after meal. The exact cause of these abnormal increases of a blood sugar level is not yet known in the art. So far, it is known that the diabetes may result in when abnormality occurs in insulin functioning to regulate metabolism of glucose. Abnormality of insulin means that the beta cells of the pancreas which secrete insulin do not sufficiently produce insulin, thereby causing an insulin-lacking state, or that, while the beta cells of the pancreas normally secrete insulin, functionality of the insulin is diminished for some reasons in such a way as not to properly regulate metabolism of glucose, thereby increasing a blood sugar level due to the so-called insulin resistance. Methods for treating the diabetes are largely classified into diet, exercise, medicinal therapy, insulin injection, and pancreatic grafting.

Insulin injection is a treatment method used to an insulin-dependent diabetic patient but takes effect also on a non-insulin-dependent diabetic patient. When carrying out the insulin injection method, while it is a norm that insulin is injected once or twice a day, an amount of insulin secreted in the human body is not constant, that is, secretion of insulin is increased three times a day before and after meal and decreased except those times. Therefore, in the insulin injection method in which an amount of insulin corresponding to an average insulin secretion amount of the human body can not but be injected once or twice a day, insulin becomes deficient after meal to induce a hyperglycemic state but excessive in the night to induce a hypoglycemic state. Consequently, since insulin supply is abnormal, a health condition of the human body cannot but be deteriorated. Accordingly, it is to be readily understood that the existing insulin injection method cannot supply changing amounts of insulin in conformity with changes in the insulin secretion as in a normal person and therefore cannot be of help to the prevention of diabetes complications. Accordingly, as improved diabetes treatment techniques, there are disclosed in the art a portable insulin pump in which an insulin injection amount is adjusted by a computer to conform to the insulin secretion of a normal person, and a method for grafting beta cells of the pancreas.

Generally, an automatic syringe device (also called as an insulin pump, insulin syringe device, automatic insulin syringe device, and so forth) used or prolonged injection of liquid has a configuration in which push means for pushing a syringe piston is coupled to a housing accommodating an injection syringe. This type of automatic syringe device is disclosed in Japanese Utility Model Laid-open Publication No. Sho 52-3292 and U.S. Pat. No. 4,417,889. However, since this type of automatic syringe device is complicated in use, inconvenience is caused when an old or feeble person manipulates the automatic syringe device.

In order to solve such a disadvantage, the present applicant disclosed in Korean Patent No. 307191 an insulin pump which is convenient to use and has a compact design. Referring to FIG. 1, in the insulin pump, when a syringe is refilled with injection liquid after use, a rotating shaft can be removed from a housing in a manner such that a precise filling height can be easily set while being viewed with the naked eye and then the rotating shaft and a push plate can be coupled in place to the housing. The insulin pump includes an injection needle unit which employs a feeding tube 1 connected to a connector 2. The injection needle unit is assembled to a housing 120 by means of a cover 110 which is sealably coupled to an upper end of the housing 120 at one side of the housing 120. Under the cover 110, a syringe 21, a piston 122, piston push means 150, power transmission means 130, and a rotating shaft 131 adapted to drive the piston push means 150 by power transmitted from the power transmission-means 130 are arranged in the housing 120. A key input unit 123 is also installed on the housing 120 and electrically connected to a control circuit provided in the housing 120 to control the power transmission means 130. A display 124 such as an LCD is also installed on the housing 120 in order to display a controlled state of the syringe device. At the other side of the housing 120, a battery cover 125 is coupled to the upper end of the housing 120 to fixedly hold a battery in the housing 120. A reset button 121 functions to generate a reset signal for the control circuit. The reference numeral 140 represents a bottom cover.

FIG. 2 is a block diagram illustrating a control circuit of the insulin pump shown in FIG. 1. The control circuit includes the key input unit 123 for generating a key signal, a control unit 170 having a microcomputer function to recognize a key input generated from the key input unit 123, the display 124 for outputting data corresponding to the recognized key input and displaying the data, and a ROM 165 for storing diverse data and programs. The control circuit also includes a motor drive unit 167 for driving a motor 168 under the control of the control unit 170 while controlling a rotating speed of the motor 168, and a photocoupler 169 for sensing the rotating speed of the motor 168. Preferably, the control unit 170 includes a pair of controllers, that is, a first controller 171 and a second controller 172, which have the same function, in order to maintains a desired function even when one of the controllers 171 and 172 is out of order. The controllers 171 and 172 have terminals P1 to P5 and terminals P1' and P2", respectively. These terminals are ports connected to data and/or bus lines, respectively. The motor 168 may be a stepping motor or a servo motor.

FIG. 3 is a cross-sectional view illustrating a blood sugar level measuring device 200 according to the conventional art. The blood sugar level measuring device 200 includes a measuring lamp 211 for measuring a blood sugar level, a control unit 210 for controlling the measuring lamp 211', recognizing a blood sugar level inputted from the measuring lamp 211 and conducting appropriate signal conversions, a housing 223 having a lamp hole 221 through which the measuring lamp 211 is fitted and an insertion groove 222 into which a measuring probe 230 is inserted, and a fixing protrusion 224 which is spring-biased in the housing 223 to fixedly hold the measuring probe 230 inserted into the insertion groove 222. The measuring probe 230 has a fitting hole 231 into which the fixing protrusion 224 is fitted, a light passage hole 233 which is defined at a position corresponding to the measuring lamp 211 when the measuring probe 230 is inserted into the insertion groove 222, and a measuring plate 235 which closes one end of the light passage hole 233. The reference numeral 240 represents a base member to which the housing 223 is secured.

FIG. 4 is a block diagram illustrating a control circuit of the blood sugar level measuring device shown in FIG. 3. The control circuit has a control unit 210 which functions to receive a command from a microcomputer 250 and a measurement of blood sugar level from the measuring lamp 211. The control unit 210 includes a digital/analog converter 212 for converting an output from a terminal P7 of the microcomputer 250 into an analog signal, a lamp driver 213 for driving a light emitting lamp element 211-1 of the measuring lamp 211 based on a converted signal output from the digital/analog converter 212, with the measuring lamp 211 composed of the light emitting lamp element 211-1 and a light receiving lamp element 211-2 which receives light emitted from the light emitting lamp element 211-1 and reflected by the measuring plate 235, a lamp signal receiver 214 for receiving and amplifying the light received by the light receiving lamp element 211-2 of the measuring lamp 211, and an analog/digital converter 215 for converting an output from the lamp signal receiver 214 into a digital signal and transmitting the digital signal to the terminal P7 of the microcomputer 250.

FIG. 5 is a time chart illustrating a relationship between blood sugar level and insulin injection amount with the lapse of time.

Meanwhile, as a concept of local area radio communication which replaces local area wire transmission or infrared-ray communication, the Bluetooth protocol has been proposed in the art by the company named Ericsson. While the Bluetooth communication as local area radio communication which enables two-way transmission of voice and data is expected to be widely used in the future in the field of a communication terminal, in these days, a technology for applying the Bluetooth communication method to a radio telephone by solving the problem provoked by ringing of the radio telephone at a public place has not yet been disclosed in the art. In this regard, an attempt to solve the problem is disclosed in Korean Patent No. 341988 as illustrated in FIGS. 6 and 7.

FIG. 6 is a schematic diagram illustrating a Bluetooth communication device and a radio telephone which is capable of Bluetooth radio communication with the Bluetooth communication device. The Bluetooth communication device 300 installed at a public place functions to find all radio telephones 400 which exist within a distance enabling the Bluetooth radio communication and implement through radio communication a controlling operation for intended conversion from an alarm mode into a manner mode. At this time, the Bluetooth communication device 300 serves as a master, and all radio telephones 400 which are within the distance enabling the Bluetooth radio communication serve as slaves. The radio telephones 400 which can be controlled by the Bluetooth communication device 300 must be respectively equipped with the Bluetooth modules 410 by themselves.

FIG. 7 is a block diagram illustrating a control circuit of the Bluetooth communication device 300 shown in FIG. 6. The Bluetooth communication device 300 includes an RF transmitter 310, an RF receiver 320, a baseband processor 330 and a communication controller 340. The RF transmitter 310, RF receiver 320 and baseband processor 330 constitute a transmitter/receiver unit 350.

The RF transmitter 310 modulates a data packet which is generated in the baseband processor 330 to be radio-transmitted, into a preset frequency band, and then amplifies and outputs the modulated data packet.

The RF receiver 320 maximally suppresses amplification of noise of a received frequency signal, amplifies a signal having the preset frequency band, modulates the signal to a low frequency band, and then outputs the signal having the low frequency band to the baseband processor 330.

The baseband processor 330 changes various HCI (host control interface) data packets outputted from the communication controller 340 into packet formats by adding access codes and headers to the data packets, changes again the packet formats into predetermined data packets for radio transmission, radio-transmits the predetermined data packets through the RF transmitter 310 at the preset frequency band, changes the data packets received from the RF receiver 320 into the HCI packets, and then outputs the changed HCI packets to the communication controller 340.

The communication controller 340 controls the entire operations of the Bluetooth communication device 300. When receipt of inquiry and answer messages (inquiry and answer data packets) from the radio telephones serving as the slaves, which are inputted from the baseband processors 330, is sensed, the communication controller 340 establishes connections with the respective radio telephones, and then controls the respective radio telephones to compulsorily convert the alarm mode into the manner mode.

The above-described technologies are independently used in their respective fields of use. In particular, since radio communication cannot be implemented between an insulin pump and a blood sugar measuring device, a patient should separately use the insulin pump and the blood sugar measuring device, so that inconvenience is caused to a patient who uses both of the insulin pump and the blood sugar measuring device.

Recently, a radio-control technique using a personal digital assistant (PDA) is disclosed in Korean Patent Laid-open Publication No. 2002-76202. However, in this technique, since a preset routine is simply executed using the merit of radio communication rendered by the PDA, it is difficult to perform two-way data processing in real time, and therefore, it is further difficult to apply the radio-control technique using the PDA to an insulin pump.

SUMMARY OF THE INVENTION

Accordingly, the present invention has been made in an effort to solve the problems occurring in the related art, and an object of the present invention is to provide a method for controlling an insulin pump through the Internet, wherein radio communication among an insulin pump, a blood sugar level measuring device and a PDA (personal digital assistant) is enabled through Bluetooth chips, so that the insulin pump can be operated in real time in conformity with a measurement from the blood sugar level measuring device and even an attending physician from a remote place can regulate an insulin injection amount or an insulin injection mode for a patient using the insulin pump through the Internet or the PDA under the action of a server.

In order to achieve the above object, in the present invention, Bluetooth modules (or chips) are respectively built in an insulin pump, a blood sugar level measuring device and a personal digital assistant. The Bluetooth modules transmit and receive signals by the ID through the medium of a Bluetooth communication device installed on a main board of a main unit of a computer. The main unit of the computer and the PDA are connected through the Internet with a server which functions to administrate a patient using the insulin pump. The method according to the present invention which is implemented in the server comprises a first step of ascertaining whether or not a logged-in person is a physician; a second step of receiving blood sugar level data corresponding to a patient's ID and driving the insulin pump when it is ascertained that the logged-in person is not a physician; a third step of changing the logged-in person to an attending physician when it is ascertained that the logged-in person is a physician but not an attending physician; and a fourth step of remotely commanding a new insulin injection amount based on a blood sugar level of the corresponding ID and a current insulin injection amount when it is ascertained that the logged-in person is a physician and also an attending physician.

According to the present invention, there is provided a method for controlling an insulin pump through the Internet, comprising the steps of: preparing an insulin pump, a blood sugar level measuring device and a personal digital assistant in which Bluetooth modules are built, respectively, so that the Bluetooth modules transmit and receive signals by the ID through the medium of a Bluetooth communication device installed on a main board of a main unit of a computer and that the main unit of the computer and the PDA are connected through the Internet with a server which functions to administrate a patient who uses the insulin pump; ascertaining whether or not a logged-in person is a physician; determining the logged-in person as a nurse when the logged-in person is not a physician, receiving the patient's blood sugar level data and generating a command to change an insulin injection amount; checking whether or not the logged-in person is an attending physician when the logged-in person is a physician, and changing the logged-in person to an attending physician when the logged-in person is not an attending physician; and driving a corresponding insulin pump having the patient's ID by transmitting through the Internet and the Bluetooth modules a new prescription made in consideration of a current blood sugar level measurement and insulin injection amount, when the logged-in person is an attending physician or when the logged-in person is changed to an attending physician.

BRIEF DESCRIPTION OF THE DRAWINGS

The above objects, and other features and advantages of the present invention will become more apparent after a reading of the following detailed description when taken in conjunction with the drawings, in which.

DETAILED DESCRIPTION OF PREFERRED EMBODIMENTS

Figure 1:
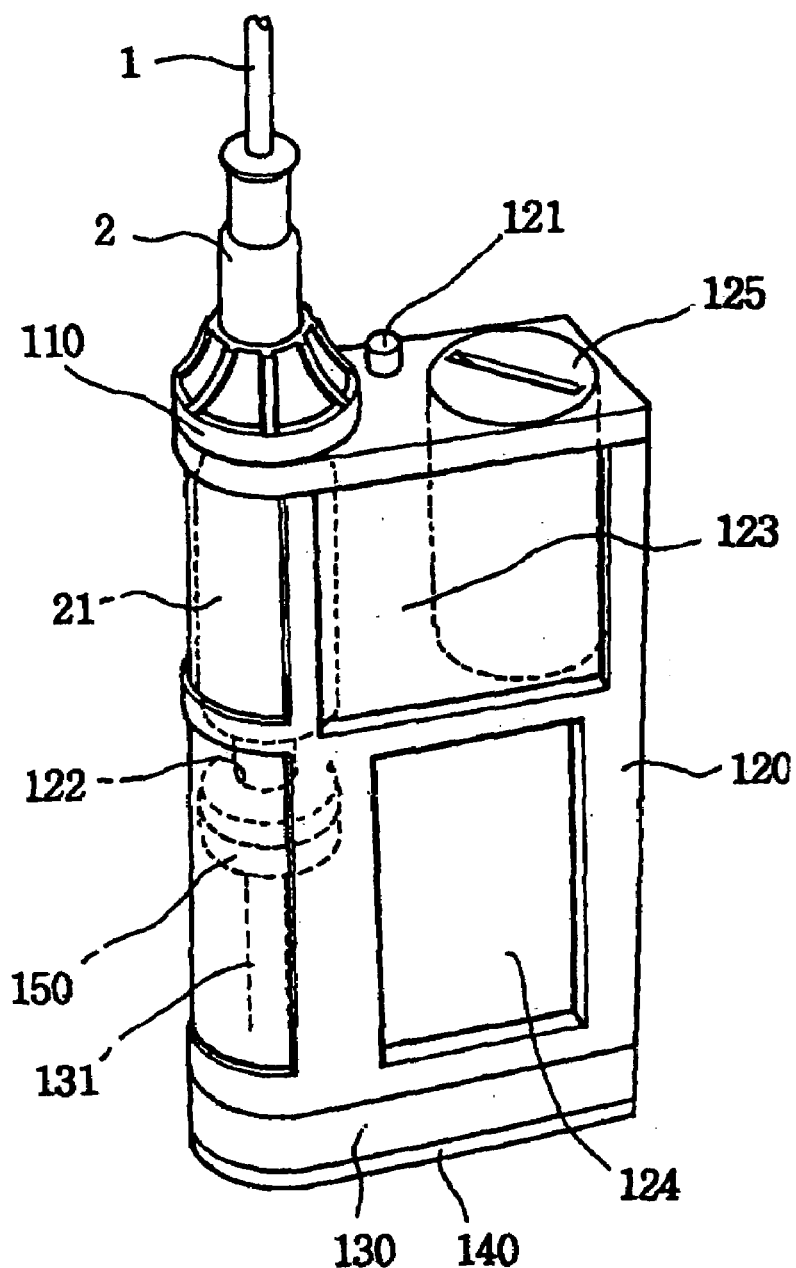
FIG. 1 is a perspective view illustrating an insulin pump to which the present invention is applied.
Figure 2:
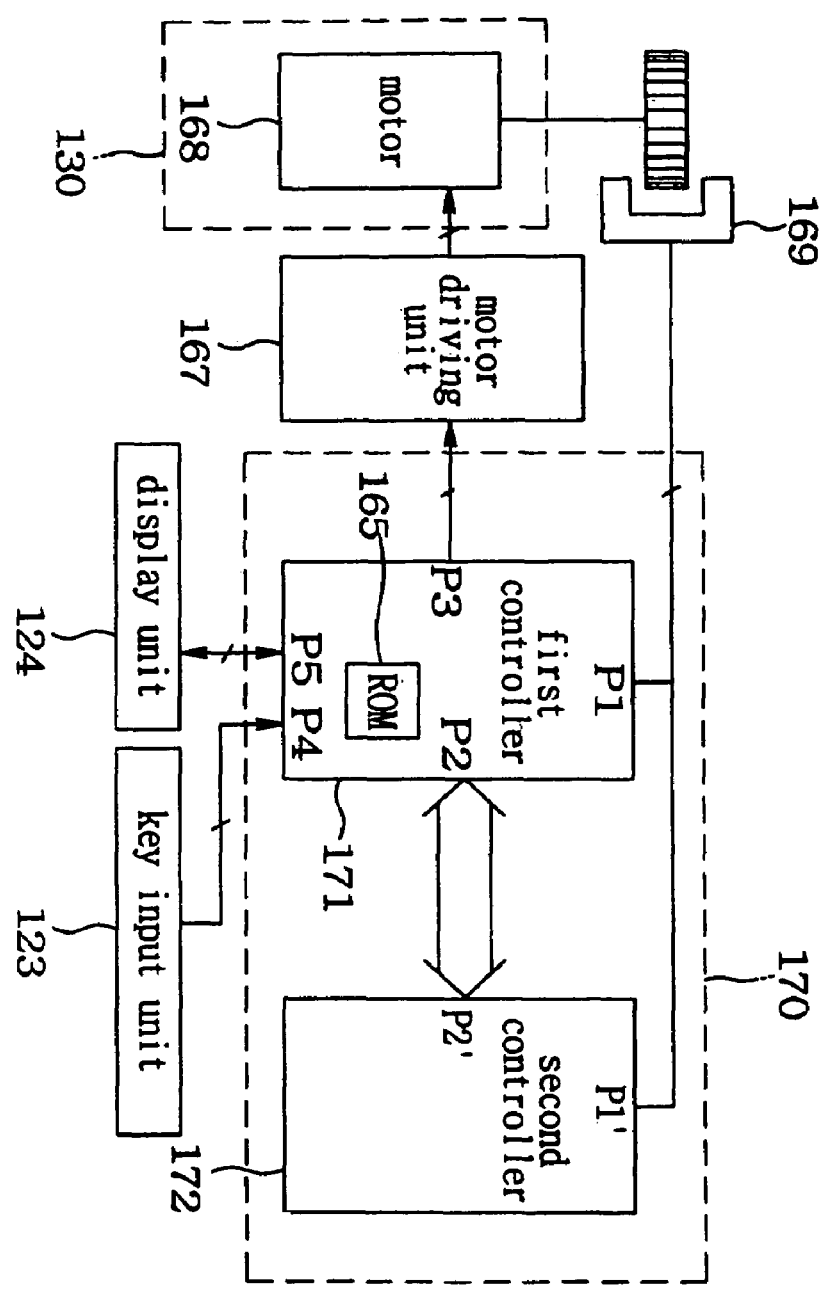
FIG. 2 is a block diagram illustrating a control circuit of the insulin pump shown in FIG. 1.
Figure 3:
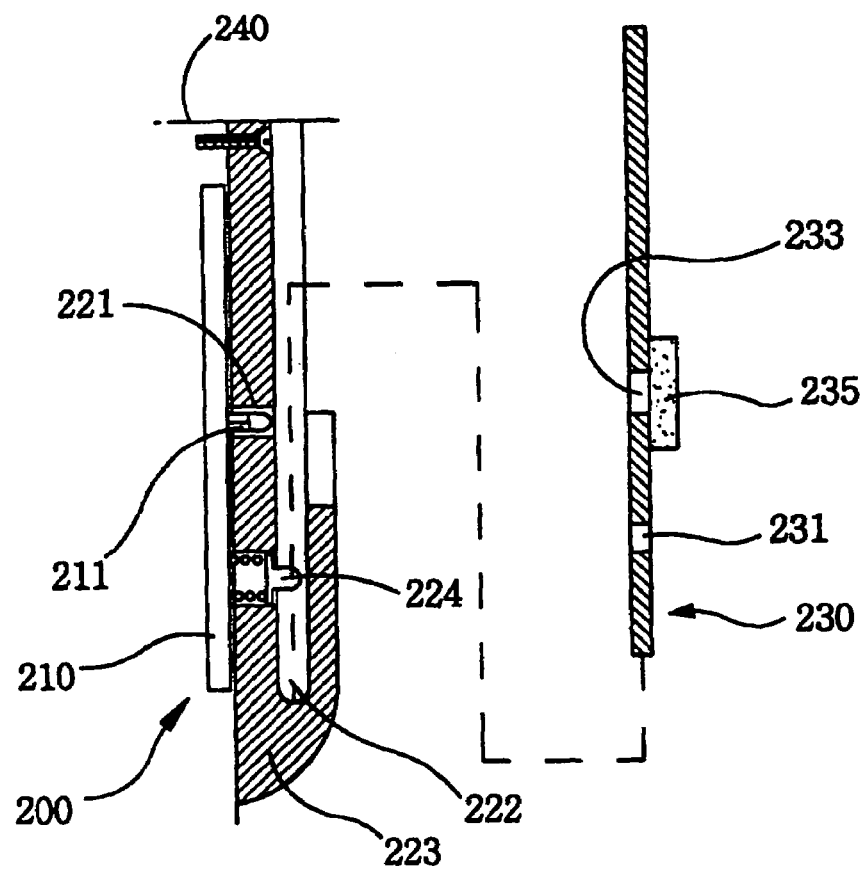
FIG. 3 is a cross-sectional view illustrating a blood sugar level measuring device according to the conventional art.
Figure 4:
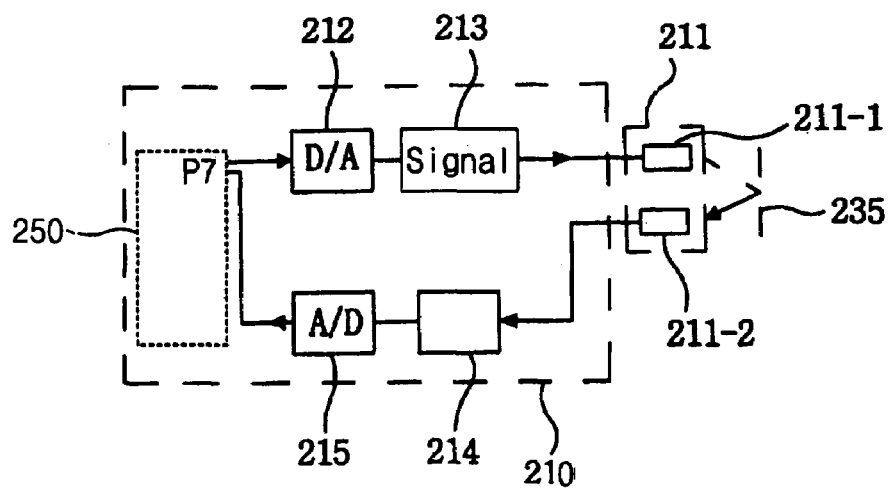
FIG. 4 is a block diagram illustrating a control circuit of the blood sugar level measuring device shown in FIG. 3.
Figure 5:
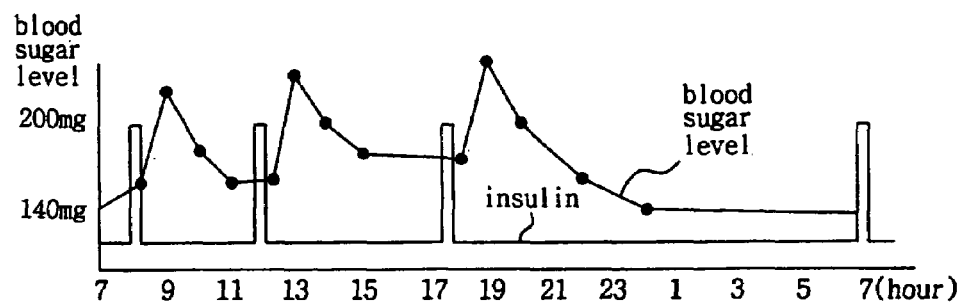
FIG. 5 is a time chart illustrating a relationship between blood sugar level and insulin injection amount with the lapse of time.
Figure 6:
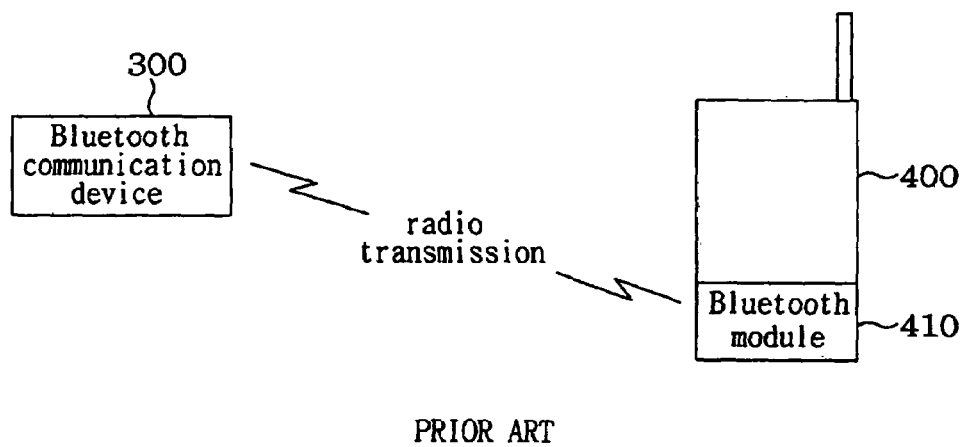
FIG. 6 is a schematic diagram illustrating a typical example of communication using the Bluetooth protocol.
Figure 7:
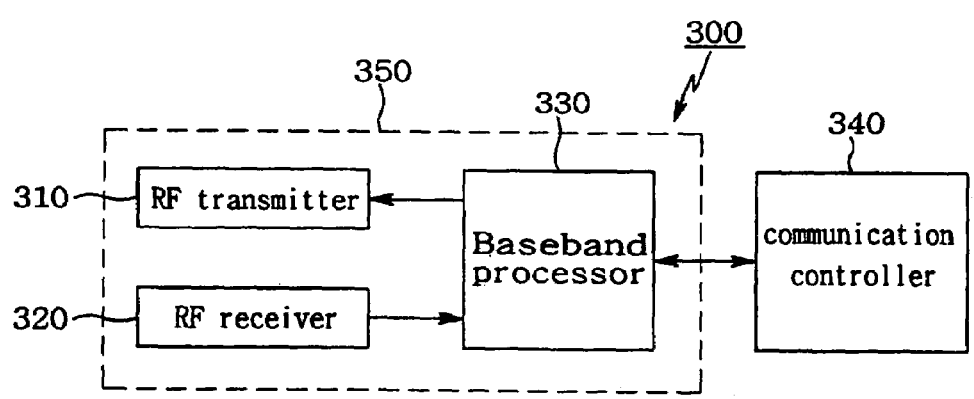
FIG. 7 is a block diagram illustrating a control circuit of a Bluetooth communication device shown in FIG. 6.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 8:
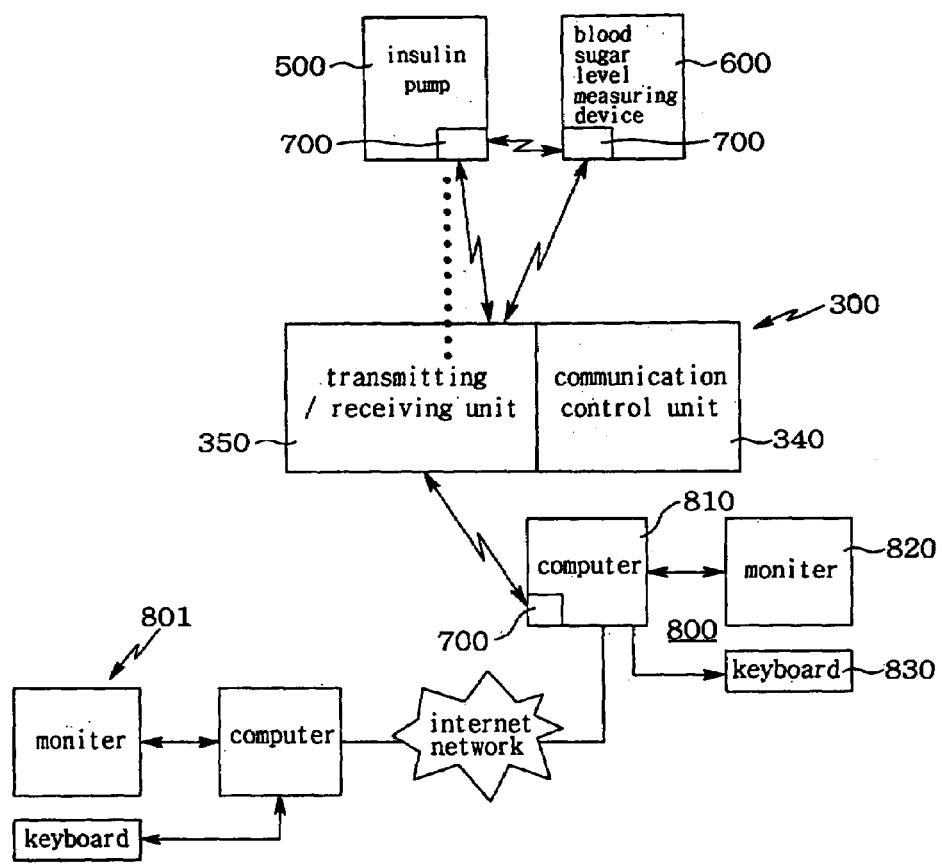
FIG. 8 is a block diagram for explaining a method for controlling an insulin pump through the Internet in accordance with an embodiment of the present invention.

FIG. 8 is a block diagram for explaining a method for controlling an insulin pump through the Internet in accordance with an embodiment of the present invention. According to the present invention, Bluetooth modules 700 are built in an insulin pump 500, a blood sugar level measuring device 600, and a radio telephone or a personal digital assistant 400, respectively. A Bluetooth communication device 300 is separately installed on a main unit 810 of a computer 800 which is used by a nurse, etc., so that the Bluetooth communication device 300 can transmit and receive a signal to and from the Bluetooth modules 700. The Bluetooth communication device 300 has a transmitting/receiving unit 350 and a communication control unit 340. The computer 800 comprises the main unit 810 in which the Bluetooth communication device 300 is installed, a monitor 820 and a keyboard 830.

The main unit 810 of the computer is connected to the Internet through a modem. A server 900 and another computer 801 which belongs to an attending physician and is capable of logging in the server 900 are also connected to the Internet. The personal digital assistant (PDA) 400 can communicate with a counter part's personal digital assistant 400' through an Internet service provider (ISP) 910 having a qualification from a mobile communication company such as of 011 and 016.

Figure 9:
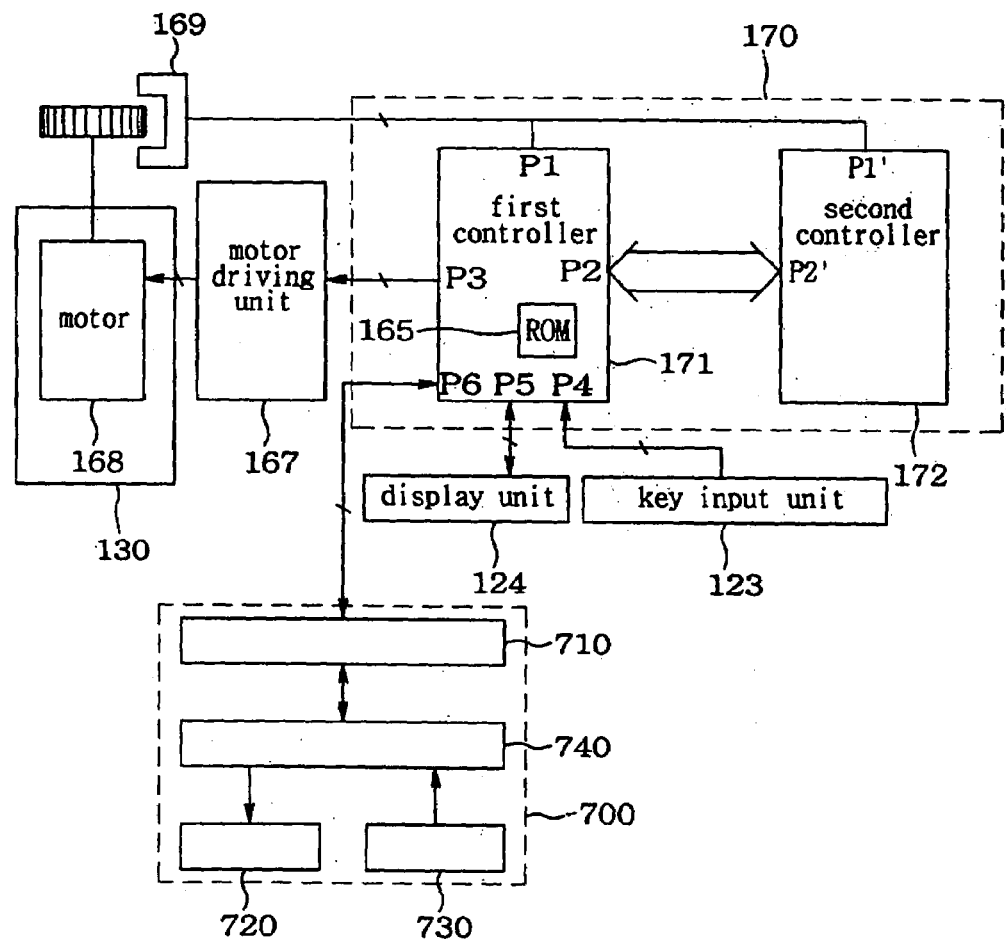
FIG. 9 is a block diagram illustrating a control circuit of an insulin pump according to the present invention.

FIG. 9 is a block diagram illustrating a control circuit of an insulin pump according to the present invention. The control circuit includes a key input unit 123 for generating a key signal to drive the insulin pump, a control unit 170 having a microcomputer function to recognize a key input generated from the key input unit 123, a display 124 for outputting data corresponding to the recognized key input and displaying the data, and a ROM 165 for storing diverse data and programs. The control circuit further includes a motor drive unit 167 for driving a motor 168 under the control of the control unit 170 while controlling a rotating speed of the motor 168 for driving a syringe piston, and a photocoupler 169 for sensing the rotating speed of the motor 168. According to the present invention, a function for recognizing and controlling the Bluetooth modules is added as a program to the control unit 170 for controlling the insulin pump. The Bluetooth module 700 is connected to a terminal of the control unit 170 to be controlled thereby.

The Bluetooth module 700 comprises a microcomputer 710, an RF transmitter 720, an RF receiver 730 and a baseband processor 740. The microcomputer 710 receives a command from the control unit 170 and transmits data to the control unit 170. The RF transmitter 720 modulates, in response to a command from the microcomputer 710, a signal which is generated by adding a header, etc. to a data packet and is transmitted from the baseband processor 740, and then, outputs an RF signal. The RF receiver 730 detects and receives a signal transmitted from another Bluetooth module 700. The baseband processor 740 changes a command (data packet) from the microcomputer 710 into a transmission data packet to be radio-transmitted, by adding a header, etc. to the command, and then, outputs the transmission data packet to the RF transmitter 720. Further, the baseband processor 740 recognizes, from a received signal, an ID and data of a transmitter, changes the received signal into a data packet, and then, outputs the changed data packet to the microcomputer 710.

Figure 10:
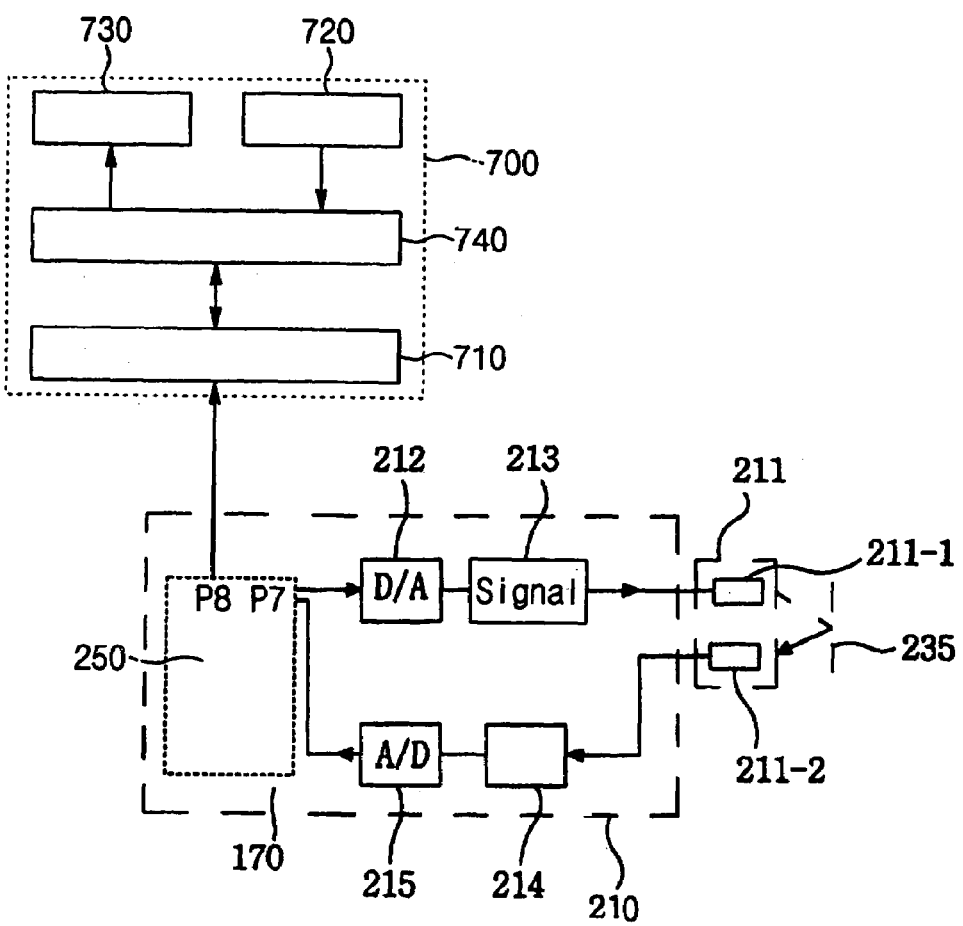
FIG. 10 is a block diagram illustrating a control circuit of a blood sugar level measuring device according to the present invention.

FIG. 10 is a block diagram illustrating a control circuit of a blood sugar level measuring device according to the present invention. The control circuit includes a microcomputer 250, a digital/analog converter 212 for driving a measuring lamp 211 in response to a command from the microcomputer 250, a lamp driver 213, a lamp signal receiver 214 for recognizing a measurement from the measuring lamp 211, and an analog/digital converter 215 for converting a signal outputted from the lamp signal receiver 214 into a digital signal and transmitting the digital signal to the microcomputer 250.

The Bluetooth module 700 is connected to a terminal P8 of the microcomputer 250. A function for transmitting and receiving data to and from the Bluetooth module 700 is added as a program to the microcomputer 250. The microcomputer 250 receives a signal from input means for driving the insulin pump. Since the Bluetooth module 700 has the same configuration as that shown in FIG. 9, further detailed description thereof will be omitted herein.

Figure 11:
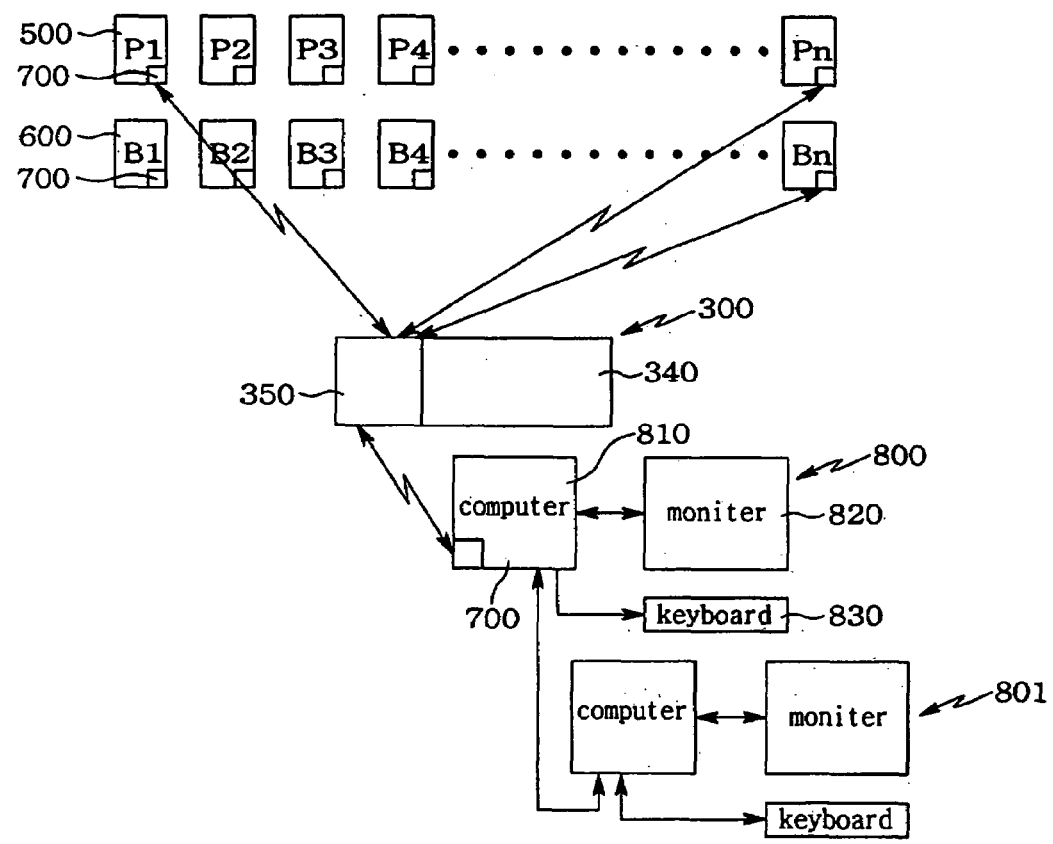
FIG. 11 is a flowchart for embodying the method according to the present invention in a server.
Figure 12:
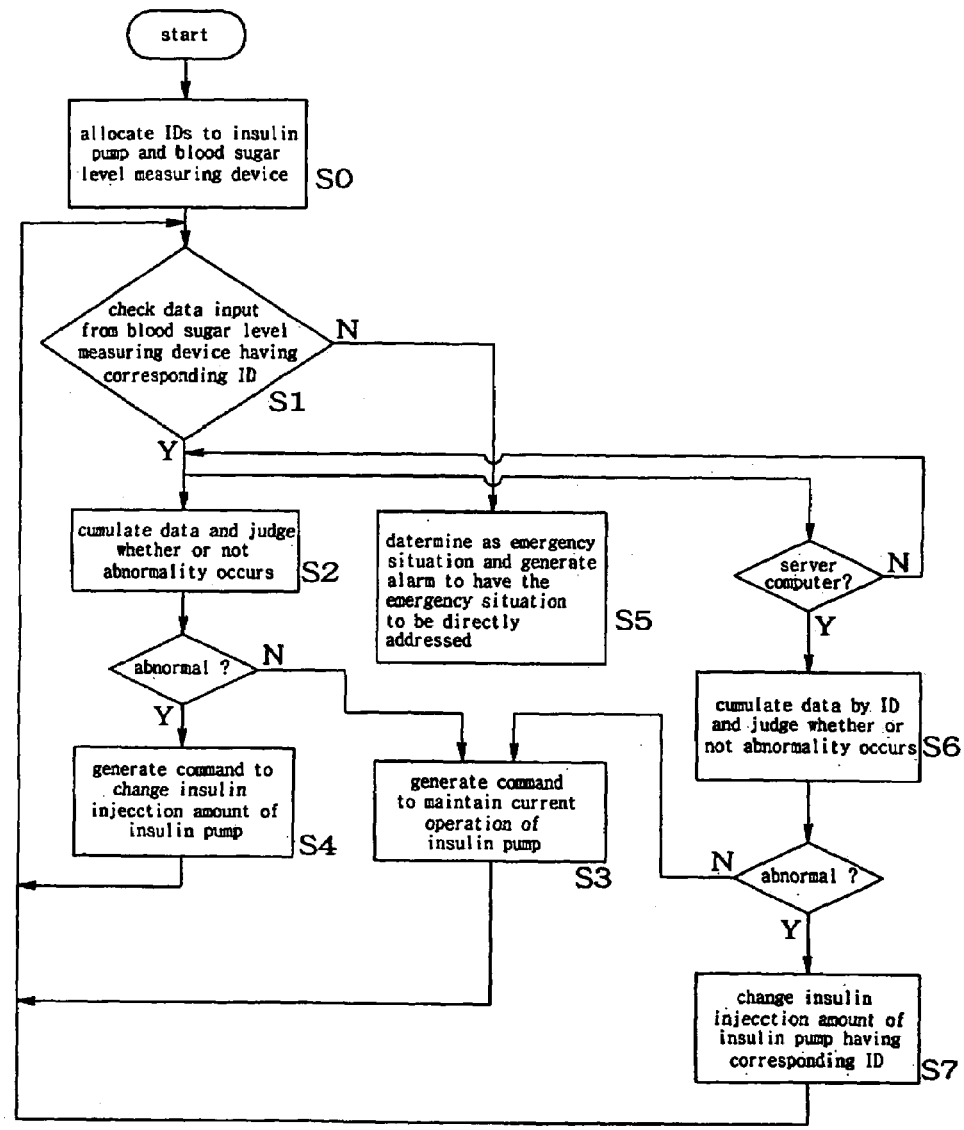
FIG. 12 is a flowchart of a program implemented in the control circuit of the insulin pump according to the present invention.
Figure 13:
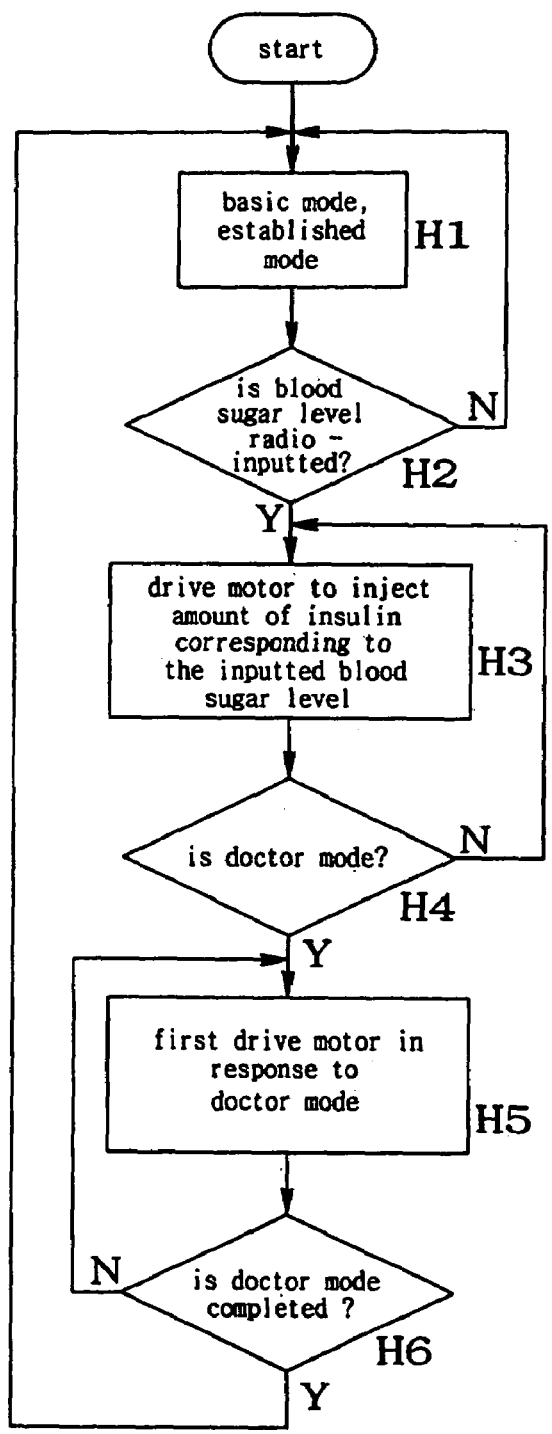
FIG. 13 is a flowchart of a program implemented in the server computer according to the present invention.

FIG. 11 is a flowchart for embodying the method according to the present invention in a server. In the method according to the present invention, first, when a person logs in the server, the server ascertains whether or not a logged-in person is a physician (S1). When the logged-in person is not a physician, the logged-in person is determined as a nurse, the patient's blood sugar level data is received, and a command to change an insulin injection amount is generated (S2). When the logged-in person is a physician, it is checked whether or not the logged-in person is an attending physician, and, when the logged-in person is not an attending physician, the logged-in person is changed to an attending physician (S3). When the logged-in person is an attending physician or when the logged-in person is changed to an attending physician, the corresponding insulin pump having the patient's ID is driven by transmitting, through the Internet and the Bluetooth modules, a new prescription made in consideration of a current blood sugar level measurement and insulin injection amount (S4).

In implementing step S2, the patient's ID and data of a registered hospital are downloaded in the server (S2-1). The patient's blood sugar level measurement data is received through classification by ID (S2-2). The corresponding prescription determined on the basis of the blood sugar level measurement data is commanded to the insulin pump which is used by the patient having the corresponding ID (S2-3). Data downloaded and uploaded to and from the blood sugar level measuring device and the insulin pump is updated and stored in real time through classification according to ID (S2-4).

In implementing step S4, data for the patient which is under treatment by the attending physician is downloaded (S4-1). It is confirmed whether or not there exists a prescription for regulating insulin injection amount, which is set and inputted by the attending physician (S4-2). The prescription is inputted to the main unit of the computer when the prescription exists (S4-3). A command is transmitted from the main unit to the insulin pump having the corresponding ID (S4-4).

In the present invention constructed as mentioned above, conventional Bluetooth modules 700 are respectively built in the insulin pump 500, the blood sugar level measuring device 600 and the personal digital assistant 400. Also, the Bluetooth communication device 300 which communicates with the insulin pump 500, the blood sugar level measuring device 600 and the personal digital assistant 400, and the computer 800 which communicates with the Bluetooth communication device 300, are provided. Further, the server 900 is connected to the main unit 810 through the modem and the Internet. The server 900 can store and recognize respective IDs of the insulin pump 500, the blood sugar level measuring device 600 and the personal digital assistant 400. By this function of the server 900, when a person logs in the server 900, the server 900 provides a corresponding program and data by recognizing the person's ID. In this way, intercommunication among a plurality of personal digital assistants 400 is enabled by the medium of the Internet service provider 910, and the personal digital assistants 400 can be connected to the server 900 to upload and download the same data.

Accordingly, referring to FIG. 11, as the personal digital assistant 400, the insulin pump 500 and the blood sugar level measuring device 600 transmit, by their IDs, data to the main unit 810 by the medium of the Bluetooth communication device 300 (while a pair of insulin pump 500 and the blood sugar level measuring device 600 are illustrated in the drawing, it is to be readily understood that a plurality of insulin pumps and blood sugar level measuring devices which are used by other patients and have their respective IDs can be used to constitute a plurality of pairs), the main unit 810 recognizes the data through a data bus of a main board, and is connected to the Internet through the modem. Then, it is possible for a person to log in the server 900 through an authentication procedure.

In this case, as a person logs in the server 900, the server 90Q ascertains whether or not a logged-in person is a physician (S1). When the logged-in person is a physician, it is checked whether or not the logged-in person is an attending physician, and, when the logged-in person is not an attending physician, the logged-in person is changed to an attending physician (S3). If it is ascertained in step S1 that the logged-in person is not a physician, the second step S2 is implemented. In step S2, the insulin pump 500 is employed. That is to say, the server 900 downloads the patient's ID and data of a registered hospital on the basis of stored IDs through the registered Bluetooth module 700 to the personal digital assistant 400 (S2-1). The patient's blood sugar level measurement data is received by ID in the server 900 (S2-2). A corresponding prescription determined on the basis of the blood sugar level measurement data from the blood sugar level measuring device 600 is commanded to the insulin pump 500 which is used by the patient having the corresponding ID (S2-3). Data downloaded and uploaded to and from the blood sugar level measuring device 600 and the insulin pump 500 is updated and stored in real time in a memory part of the server 900 through classification according to ID (S2-4). Hence, it is possible to regulate an amount of insulin injected by the insulin pump, which is suitable for a patient having a specific ID.

If the logged-in person is an attending physician in step S3, data for the patient who is under treatment by the attending physician is downloaded from the server to the main unit or the personal digital assistant (for example, as designated by the reference numeral 400') which is owned by the attending physician (S4-1). Then, it is confirmed whether or not the attending physician generates a command to change an insulin injection amount after considering the downloaded data, which command is to be transmitted to the server 900 (S4-2). If the attending physician generates the command to change an insulin injection amount, the server 900 transmits the command to the main unit 810 through the Internet (S4-3). The command is transmitted from the main unit 810 to the personal digital assistant 400 through the Bluetooth communication device 300, and then the insulin pump 500 having the corresponding ID is driven through the personal digital assistant 400 (S4-4).

As apparent from the above description, in the present invention, Bluetooth modules are respectively built in an insulin pump, a blood sugar level measuring device and a personal digital assistant. A separate server for administrating the insulin pump, blood sugar level measuring device and personal digital assistant is provided so that the insulin pump, blood sugar level measuring device and personal digital assistant are connected with the server through the Internet to be controlled thereby. Therefore, in the present invention, control through the personal digital assistant is enabled. That is to say, in a manner such that a nurse radio-transmits a patient's data to the server and an attending physician informs the patient of an insulin injection amount through the server, it is possible to remote control insulin injection for the patient in real time, through the Internet.

Further, in the present invention, IDs are allocated to a plurality of insulin pumps, blood sugar level measuring devices and personal digital assistants, so that communication among them can be controlled by a Bluetooth communication device installed on a main unit of a computer. The central Bluetooth communication device is linked with the computer having a server function to radio-receive respective blood sugar levels and command corresponding prescriptions to corresponding insulin pumps. Therefore, as a nurse supplies, to the server, data corresponding to a patient's ID, an attending physician from a remote place can control the corresponding insulin pump through the Internet or the personal digital assistant. As a consequence, it is not necessary for the attending physician to directly visit the patient. In other words, as attending physicians transmit insulin injection amounts for patients to the server all at once or one by one, the server enables control to be implemented by hospitals or patients based on the insulin injections amounts received by it, whereby patient administrating efficiency is improved and quick treatment is made possible.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method for controlling an insulin pump through the Internet, comprising the steps of:

providing an insulin pump, a blood sugar level measuring device and a personal digital assistant in which wireless communication protocol modules are built, respectively, so that the wireless modules transmit and receive signals through the medium of a wireless communication device installed on a main board of a main unit of a computer and that the main unit of the computer and the PDA are connected through the Internet with a server which sends a command to the insulin pump;

logging in as an authorized user of said server;

ascertaining whether or not a logged-in person is a physician;

determining the logged-in person as a nurse when the logged-in person is not a physician, receiving the patient's blood sugar level data and generating said command to change an insulin injection amount;

checking whether or not the logged-in person is an attending physician when the logged-in person is a physician, and changing the logged-in person to an attending physician when the logged-in person is not an attending physician; and driving said insulin pump corresponding to a patient's ID by transmitting through the Internet and the modules a new prescription made in consideration of a current blood sugar level measurement and insulin injection amount, when the logged-in person is an attending physician or when the logged-in person is changed to an attending physician.

2. The method as set forth in claim 1, wherein the determining step comprises the sub steps of:

downloading the patient's ID and data of a registered hospital;

receiving the patient's blood sugar level measurement data through classification according to said patients ID;

commanding a corresponding prescription determined on the basis of the blood sugar level measurement data, to the insulin pump which is used by the patient having the corresponding patients ID; and updating and storing data downloaded and uploaded to and from the blood sugar level measuring device and the insulin pump, in real time through classification according to the patients ID.

3. The method as set forth in claim 1, wherein the driving step comprises the sub steps of:

downloading data for the patient which is under treatment by the attending physician;

confirming whether or not there exists a prescription regarding insulin injection amount which is set and inputted by the attending physician;

inputting the prescription to the main unit of the computer when the prescription exists; and transmitting a command from the main unit to the insulin pump having the corresponding patients ID.

* * * * *